(12) United States Patent
Kropf et al.

(10) Patent No.: US 9,926,258 B2
(45) Date of Patent: Mar. 27, 2018

(54) PHOTOLABILE PRO-FRAGRANCES

(71) Applicant: Henkel AG & Co. KGaA, Duesseldorf (DE)

(72) Inventors: Christian Kropf, Hilden (DE); Thomas Gerke, Duesseldorf (DE); Ursula Huchel, Cologne (DE); Axel Griesbeck, Cologne (DE); Agnieszka Landes, Bergheim (DE)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 15/232,125

(22) Filed: Aug. 9, 2016

(65) Prior Publication Data

US 2016/0347704 A1 Dec. 1, 2016

Related U.S. Application Data

(63) Continuation of application No. PCT/EP2015/053502, filed on Feb. 19, 2015.

(30) Foreign Application Priority Data

Feb. 24, 2014 (DE) ........................ 10 2014 203 252

(51) Int. Cl.
| | |
|---|---|
| *C07C 69/716* | (2006.01) |
| *A61K 8/37* | (2006.01) |
| *A61Q 5/02* | (2006.01) |
| *A61Q 13/00* | (2006.01) |
| *A61Q 19/10* | (2006.01) |
| *C07C 69/738* | (2006.01) |
| *C11B 9/00* | (2006.01) |
| *C11D 3/50* | (2006.01) |

(52) U.S. Cl.
CPC .............. *C07C 69/716* (2013.01); *A61K 8/37* (2013.01); *A61Q 5/02* (2013.01); *A61Q 13/00* (2013.01); *A61Q 19/10* (2013.01); *C07C 69/738* (2013.01); *C11B 9/0061* (2013.01); *C11D 3/50* (2013.01); *C07C 2601/14* (2017.05); *C07C 2601/16* (2017.05)

(58) Field of Classification Search
CPC . C07C 69/716; C07C 69/738; C07C 2101/14; C07C 2101/16; C11D 3/50; C11B 9/0061; A61K 8/37; A61Q 5/02; A61Q 13/00; A61Q 19/10
See application file for complete search history.

(56) References Cited

U.S. PATENT DOCUMENTS

| 4,325,962 A | 4/1982 | Rainer |
| 6,949,680 B2 | 9/2005 | Herrmann |
| 8,129,569 B2 | 3/2012 | Huchel et al. |
| 8,604,250 B2 | 12/2013 | Gerke et al. |
| 2011/0257014 A1 | 10/2011 | Jakobi et al. |

FOREIGN PATENT DOCUMENTS

| WO | 2006/023864 A1 | 3/2006 |
| WO | 2008/069609 A1 | 6/2008 |
| WO | 2009/055917 A1 | 5/2009 |

OTHER PUBLICATIONS

PCT International Search Report (PCT/EP2015/053502) dated Apr. 14, 2015.
Duus, "The Acid Catalysed Reaction of 1,4-diketones with Hydrogen Sulphide; A Convenient Route to Substituted Thiophens", XP002738468, Tetrahedron, vol. 32, pp. 2817-2825, 1976.
Chow et al., "The Photocycloaddition of Dibenzolymethanatoboron Difluoride (DBMBF2) with Conjugated Enones and En-esters", XP002738470, Canadian Journal of Chemistry, vol. 71, pp. 846-854, 1993.
Hoffman et al., "A New Chiral Alkylation Methodology for the Synthesis of 2-Alkyl-4-Ketoacids in High Optical Purity Using 2-Triflyfoxy Esters", XP002737471, Tetrahedron Letters, vol. 34, No. 13, pp. 2051-2054, 1993.
Kraus et al., "Michael Addition Reactions of a-acyloxy Nitrile Anions", XP004185407, Tetrahedron Letters, vol. 41, pp. 21-24, 2000.
Liu et al., "Iron-Catalyzed Oxidation of Tertiary Amines: Synthesis of B-1,3-Dicarbonyl Aldehydes by Three-Component C-C Couplings", XP002738469, Organic Letters, vol. 13, No. 23, pp. 6272-6275, 2011.

*Primary Examiner* — Sudhakar Katakam

(74) *Attorney, Agent, or Firm* — P. Scott Smith

(57) ABSTRACT

The invention relates to specific ketones of formula (I) which act as photolabile pro-fragrances. The invention further relates to detergents or cleaning agents, cosmetic agents and air freshening products including ketones of said type. The invention also relates to a method for lastingly scenting surfaces and a method for lastingly fragrancing rooms using said ketones.

16 Claims, No Drawings

PHOTOLABILE PRO-FRAGRANCES

FIELD OF THE INVENTION

The present invention generally relates to the field of pro-fragrances, as are used for example in the field of detergents or cleaning agents, cosmetic agents and air freshening products, and more particularly relates to specific ketones that act as photolabile pro-fragrances. The present invention further relates to detergents or cleaning agents, cosmetic agents and air freshening products including ketones of said type. The invention also relates to a method for lastingly scenting surfaces and a method for lastingly fragrancing rooms.

BACKGROUND OF THE INVENTION

Detergents or cleaning agents, or cosmetic agents usually include fragrances that provide said agents with a pleasant smell. The fragrances usually mask the smell of the other ingredients so that the consumer perceives a pleasant smell.

In particular in the field of detergents, fragrances are important constituents of the composition, since the laundry should smell as pleasant and fresh as possible both when wet and when dry. When using fragrances, the main problem faced is that these are more or less highly volatile compounds, yet a lasting fragrance effect is sought nevertheless. In particular in the case of scents that constitute the fresh and light notes of the perfume and evaporate particularly quickly on account of their high vapor pressure, the desired longevity of the perceived fragrant smell is hardly attainable.

A delayed fragrance release can be provided for example by carrier-bonded use of fragrances. A carrier-bonded preliminary form of a fragrance is also referred to as a "pro-fragrance". In this context, patent document U.S. Pat. No. 6,949,680 discloses the use of specific phenyl ketones or pyridyl ketones as photoactivatable substances that release a terminal alkene as active substance in the presence of light in a photochemical fragmentation. Said active substance for example has a fragrancing or antimicrobial activity that is initially delayed by the photochemically induced decomposition and is released over a relatively long period of time on a specific surface.

WO 2009/118219 A1 discloses photoactivatable substances which enable a release of cyclic terpenes or cyclic terpenoids.

WO 2011/101180 discloses the use of specific ketones as photoactivatable substances that release an active substance in the presence of light in a photochemical fragmentation. Said active substance for example has a fragrancing activity which is initially delayed by photochemically induced decomposition and is released over a relatively long period of time on a specific surface.

The object of the present invention was that of providing photoactivatable substances as pro-fragrances which allow the delayed release of aromatic ketones, in particular of damascones.

Furthermore, other desirable features and characteristics of the present invention will become apparent from the subsequent detailed description of the invention and the appended claims, taken in conjunction with this background of the invention.

BRIEF SUMMARY OF THE INVENTION

A compound of general formula (I)

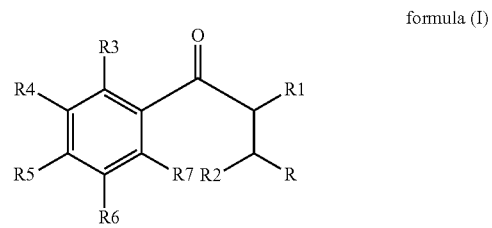

formula (I)

wherein R is a substituted hydrocarbon group, preferably having 2 to 20 C atoms, which has at least one C=O group or an ester group, preferably a C=O group; R1 is —COX; R2 is hydrogen, a halogen atom, an aryl group, —NO$_2$, a linear or branched, substituted or unsubstituted alkoxy group having up to 15 C atoms, or a linear or branched, substituted or unsubstituted alkenyl group having up to 15 C atoms, or a linear or branched or substituted or unsubstituted alkyl group having up to 15 C atoms; R3, R4, R5, R6 and R7, independently of one another, are hydrogen, a halogen atom, an amino group, —NO$_2$, —NH alkyl, —N(alkyl)$_2$, a linear or branched, substituted or unsubstituted alkoxy group having up to 15 C atoms, or a linear or branched, substituted or unsubstituted alkyl group having up to 15 C atoms, a cycloalkyl group, an acyl group, an aryl group, —OH, —COY group, or a quaternary ammonium group of formula (II)

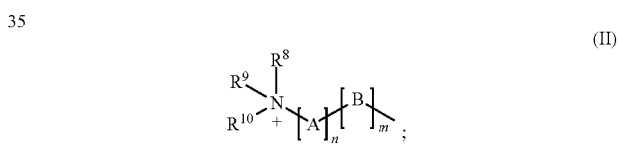

(II)

X is H, —R11, —OR11, —NR11R12, —SR11 or halogen, preferably is —OR11; Y is hydrogen, alkyl, cycloalkyl, aryl, acyl, —OH, —Oalkyl, —NH$_2$, NH-alkyl, —N(alkyl)$_2$ or halogen, A is a CH$_2$ group or a CH$_2$CH$_2$O group with n=1 to 20; B is oxygen with m=0 or 1, wherein m=0 when A is a CH$_2$CH$_2$O group; R8, R9 and R10, independently of one another, are H or a substituted or unsubstituted group including alkyl, cycloalkyl, alkenyl, aryl or acyl groups, and wherein two of the groups R8, R9 and R10 can be interconnected by ring closure; and R11 and R12, independently of one another, are hydrogen, a linear or branched, substituted or unsubstituted alkyl, aryl, alkylaryl, arylalkyl or alkenyl group, which can all optionally contain heteroatoms, preferably 1-3 heteroatoms selected from N, O and S, and preferably are a (CH(R13)CH(R14)O)$_p$—R15 group with p=1-20 and wherein R13, R14 and R15, independently of one another, are hydrogen, or a linear or branched, substituted or unsubstituted alkyl group.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

This object of the present invention was achieved by a compound of general formula (I),

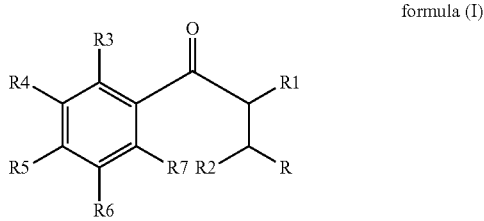

formula (I)

wherein in this formula (I)
R is a substituted hydrocarbon group, preferably having 2 to 20 C atoms, which has at least one C=O group or an ester group, preferably a C=O group;
R1 is —COX;
R2 is hydrogen, a halogen atom, an aryl group, —$NO_2$, a linear or branched, substituted or unsubstituted alkoxy group having up to 15 C atoms, or a linear or branched, substituted or unsubstituted alkenyl group having up to 15 C atoms, or a linear or branched or substituted or unsubstituted alkyl group having up to 15 C atoms;
R3, R4, R5, R6 and R7, independently of one another, are hydrogen, a halogen atom, an amino group, —$NO_2$, —NH alkyl, —N(alkyl)$_2$, a linear or branched, substituted or unsubstituted alkoxy group having up to 15 C atoms, or a linear or branched, substituted or unsubstituted alkyl group having up to 15 C atoms, a cycloalkyl group, an acyl group, an aryl group, —OH, —COY group, or a quaternary ammonium group of formula (II)

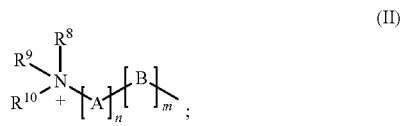

(II)

X is H, —R11, —OR11, —NR11R12, —SR11 or halogen, preferably is —OR11;
Y is hydrogen, alkyl, cycloalkyl, aryl, acyl, —OH, —Oalkyl, —$NH_2$, —NH alkyl, —N(alkyl)$_2$ or halogen,
A is a $CH_2$ group or a $CH_2CH_2O$ group with n=1 to 20;
B is oxygen with m=0 or 1, wherein m=0 when A is a $CH_2CH_2O$ group;
R8, R9 and R10, independently of one another, are H or a substituted or unsubstituted group including alkyl, cycloalkyl, alkenyl, aryl or acyl groups, and wherein two of the groups R8, R9 and R10 can be interconnected by ring closure; and
R11 and R12, independently of one another, are hydrogen, a linear or branched, substituted or unsubstituted alkyl, aryl, alkylaryl, arylalkyl or alkenyl group, which can all optionally contain heteroatoms, preferably 1-6 heteroatoms selected from N, O and S, and preferably are a $(CH(R13)CH(R14)O)_p$ R15 group with p=1-20 and wherein R13, R14 and R15, independently of one another, are hydrogen, or a linear or branched, substituted or unsubstituted alkyl group.

In the sense of the present invention, carbonyl compounds of the general formulas —(C=O)—X and —(C=O)—Y are understood to be groups —COX and —COY, wherein the groups —X and —Y are defined as described above.

It has surprisingly been found that the ketones according to the invention are particularly effective pro-fragrances which allow the delayed release of aromatic ketones, in particular damascones. The use of the ketones according to the invention in detergents, cleaning agents or care products leads to an improved long-term fragrance effect, in particular in conjunction with the textile treatment. For example, with the use of ketones according to the invention in a laundry treatment agent, such as detergent and fabric softener, an improved long-term fragrance effect of the treated laundry is found. Corresponding products also have a particularly good storage stability. The agents according to the invention additionally make it possible to reduce the total amount of perfume that is included in the agent and yet still attain olfactory advantages on the washed textiles, in particular in terms of the perception of freshness.

The ketone according to the invention according to general formula (I) is suitable as a pro-fragrance for all conventional aromatic ketones, in particular selected from buccoxime; iso jasmone; methyl beta naphthyl ketone; musk indanone; tonalid/musk plus; alpha damascone, beta damascone, delta damascone, gamma damascone, damascenone, damarose, methyl dihydrojasmonate, menthone, carvone, camphor, fenchone, alpha ionone, beta ionone, gamma methyl ionone referred to as ionone, fleuramone, dihydrojasmone, cis-jasmone, iso-E-Super, methyl cedrenyl ketone or methyl cedrylone, acetophenone, methyl-acetophenone, para methoxy acetophenone, methyl beta naphthyl ketone, benzyl acetone, benzophenone, para hydroxyl phenyl butanone, celery ketone or livescone, 6-isopropyldecahydro-2-naphtone, dimethyl octenone, freskomenthe, 4-(1-ethoxyvinyl)-3,3,5,5,-tetramethylcyclohexanone, methyl heptenone, 2-(2-(4-methyl-3-cyclohexen-1-yl)propyl)-cyclopentanone, 1-(p-menthen-6(2)-yl)-1-propanone, 4-(4-hydroxy-3-methoxyphenyl)-2-butanone, 2-acetyl-3,3-dimethyl-norbornane, 6,7-dihydro-1,1,2,3,3-pentamethyl-4 (5H)-indanone, 4-damascol, dulcinyl or cassione, gelsone, hexalon, isocyclemone E, methyl cyclocitrone, methyl-lavender ketone, orivon, para tertiary butyl cyclohexanone, verdone, delphone, muscone, neobutenone, plicatone, veloutone, 2,4,4,7-tetramethyl-oct-6-en-3-one, tetrameran, or mixtures thereof. The ketones can preferably be selected from damascones, carvone, gamma-methyl ionone, iso-E-Super, 2,4,4,7-tetramethyl-oct-6-en-3-one, benzyl acetone, damascenone, methyl dihydrojasmonate, methyl cedrylone, hedione, and mixtures thereof. All damascones and also damascenones are most preferred. The stored ketones can be released by influence of light comprising the wavelengths from 200 to 600 nm.

In accordance with a preferred embodiment of the invention the substituent R2 in formula (I) is a linear or branched, substituted or unsubstituted alkyl group having up to 6 C atoms, preferably up to 3 C atoms, and in particular is a methyl group.

In accordance with a further preferred embodiment of the invention the substituents R3, R4, R5, R6 and R7 in formula (I), independently of one another, are hydrogen or a linear or branched, substituted or unsubstituted alkoxy group having up to 6 C atoms or a linear or branched, substituted or unsubstituted alkyl group having up to 6 C atoms.

In different embodiments, alkyl in the definition of Y and in the groups —Oalkyl, —NH alkyl, and —N(alkyl)$_2$ is a linear or branched, substituted or unsubstituted alkyl group, preferably having up to 15 C atoms. Cycloalkyl denotes corresponding cyclic alkyl groups, preferably having 3 to 15

C atoms. Aryl preferably denotes a substituted or unsubstituted aryl group, preferably C6-C14 aryl, wherein one or more of the ring C atoms optionally can be replaced by heteroatoms, such as O, S or N, and can thus form a heteroaryl group. Acyl preferably denotes —C(O)alkyl, wherein alkyl is as defined above.

In accordance with a preferred embodiment of the invention ketones corresponding to the following formula (III) are particularly preferred:

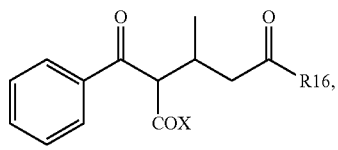
(III)

wherein

R16 is a hydrocarbon group having at least 5 C atoms, which in particular comprises a cyclic, optionally substituted hydrocarbon group, preferably a cyclic, substituted alkenyl group, in particular

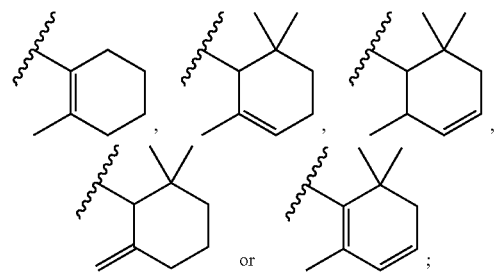

X is H, —R11, —OR11, —NR11R12, —SR11 or halogen, preferably is —OR11; and

R11 and R12, independently of one another, are hydrogen, a linear or branched, substituted or unsubstituted alkyl or alkenyl group having up to 20 C atoms, an aryl group having 6 to 14 C atoms, alkylaryl or arylalkyl group, wherein alkyl and aryl are as defined above, and preferably are a linear or branched, unsubstituted alkyl group having up to 16 C atoms, or are a $(CH(R13)CH(R14)O)_p$ R15 group with p=1-20 and R13, R14 and R15, independently of one another, are hydrogen, or a linear or branched, substituted or unsubstituted alkyl group, preferably are a $(CH(R13)CH(R14)O)_p$ R15 group with p=1-10 and R13, R14 and R15, independently of one another, are hydrogen, methyl or ethyl.

In accordance with a further embodiment of the invention, ketones corresponding to the following formulas (IV), (V), (VI), (VII), (VIII), (IX) and (X) are particularly preferred

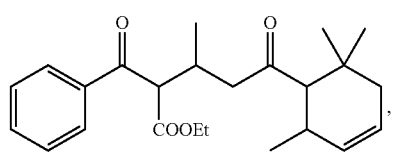
(IV)

-continued

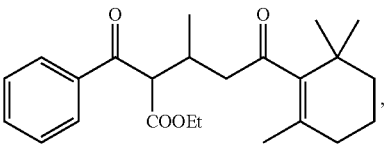
(V)

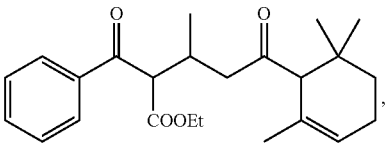
(VI)

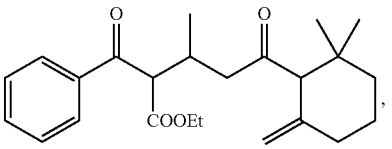
(VII)

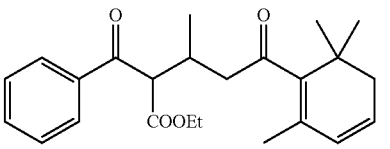
(VIII)

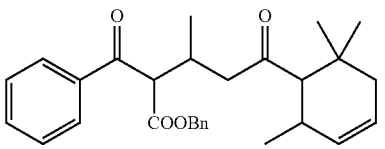
(IX)

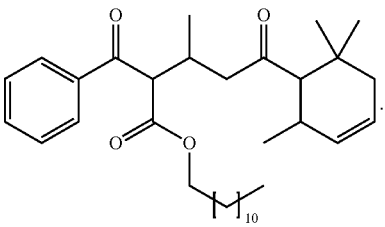
(X)

The ketones according to the invention can be incorporated in a stable manner into the conventional detergent or cleaning agent matrices, into cosmetics and existing scent compositions. They enable a delayed release of the stored fragrances, specifically of damascones in the alpha, beta, gamma or delta form and also of damascenones, in particular delta damascenones. These ketones provide conventional detergents or cleaning agents and also cosmetics with a particularly long-lasting perceived freshness. In particular, the dried, washed textile benefits from the good long-term fresh fragrance effect. The stored scent is released slowly under the influence of light (electromagnetic radiation) comprising the wavelengths from 200 to 600 nm, as illustrated in a simplified manner in the following reaction equation:

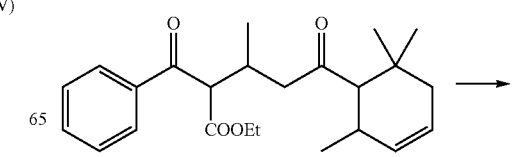

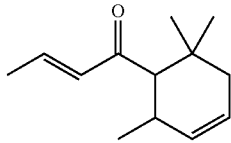

The present invention also relates to a detergent or cleaning agent, preferably a detergent, fabric softener or auxiliary washing product, including at least one ketone according to the invention, wherein said ketone is included preferably in amounts between 0.0001 and 5% by weight, advantageously between 0.001 and 4% by weight, more advantageously between 0.01 and 3% by weight, in particular between 0.1 and 2% by weight, in each case in relation to the total agent. Suitable cleaning agents are, for example, cleaning agents for hard surfaces, such as preferably dishwashing detergents. The agents according to the invention may also be cleaning agents such as household cleaners, all-purpose cleaners, window cleaners, floor cleaners, etc. The agents according to the invention may preferably be products for cleaning toilet bowls and urinals, and advantageously may be products that hang inside the toilet bowl and clean with each flush.

In accordance with a preferred embodiment of the invention the detergent or cleaning agent according to the invention includes at least one surfactant, selected from anionic, cationic, non-ionic, zwitterionic or amphoteric surfactants, or mixtures thereof.

In accordance with a further preferred embodiment of the invention the agent according to the invention is present in solid or liquid form.

The invention also relates to a cosmetic agent including at least one ketone according to the general formula (I), said cosmetic agent including said ketone preferably in amounts between 0.0001 and 5% by weight, advantageously between 0.001 and 4% by weight, more advantageously between 0.01 and 3% by weight, in particular between 0.1 and 2% by weight, in each case in relation to the total agent.

The invention also relates to an air freshening product (room air freshener, room deodorant, room spray, etc.) including at least one ketone according to general formula (I), wherein said ketone is included preferably in amounts between 0.0001 and 50% by weight, advantageously between 0.001 and 5% by weight, more advantageously between 0.01 and 3% by weight, in particular between 0.1 and 2% by weight, in each case in relation to the total agent.

In accordance with a further preferred embodiment of the invention additional fragrances are included in an agent according to the invention (i.e. detergent or cleaning agent, cosmetic agent, or air freshening product), said additional fragrances being selected in particular from the group comprising fragrances of natural or synthetic origin, preferably highly volatile fragrances, fragrances having a high boiling point, solid fragrances and/or adherent fragrances.

Adherent scents that can be used with preference within the scope of the present invention are, for example, essential oils such as *angelica* root oil, anise oil, *arnica* flower oil, basil oil, bay oil, bergamot oil, champaca flower oil, silver fir oil, silver fir cone oil, elemi oil, *eucalyptus* oil, fennel oil, fir needle oil, *galbanum* oil, geranium oil, gingergrass oil, guaiacwood oil, balsam gurjun oil, helichrysum oil, ho oil, ginger oil, iris oil, cajeput oil, calamus oil, chamomile oil, camphor oil, *cananga* oil, cardamom oil, *cassia* oil, pine needle oil, balsam copaiva oil, coriander oil, curled peppermint oil, caraway oil, cumin oil, lavender oil, lemongrass oil, lime oil, mandarin oil, melissa oil, ambrette seed oil, myrrh oil, clove oil, neroli oil, niaouli oil, olibanum oil, orange oil, oregano oil, palmarosa oil, patchouli oil, Peru balsam oil, petitgrain oil, pepper oil, peppermint oil, pimento oil, pine oil, rose oil, rosemary oil, sandalwood oil, celery oil, spike lavender oil, star anise oil, turpentine oil, *thuja* oil, thyme oil, *verbena* oil, vetiver oil, juniper berry oil, wormwood oil, wintergreen oil, ylang-ylang oil, hyssop oil, cinnamon oil, cinnamon leaf oil, citronella oil, lemon oil, and cypress oil.

However, higher boiling-point or solid scents of natural or synthetic origin can also be used within the scope of the present invention as adherent scents or scent mixtures, i.e. fragrances. These compounds include the compounds listed below and mixtures thereof: ambrettolide, alpha amylcinnamaldehyde, anethole, anisaldehyde, anisyl alcohol, anisole, anthranilic acid methyl ester, acetophenone, benzyl acetone, benzaldehyde, benzoic acid ethyl ester, benzophenone, benzyl alcohol, benzyl acetate, benzyl benzoate, benzyl formate, benzyl valerate, borneol, bornyl acetate, alpha bromostyrene, n-decyl aldehyde, n-dodecyl aldehyde, eugenol, eugenol methyl ether, eucalyptol, farnesol, fenchone, fenchyl acetate, geranyl acetate, geranyl formate, heliotropin, heptyne carboxylic acid methyl ester, heptaldehyde, hydroquinone dimethyl ether, hydroxycinnamaldehyde, hydroxycinnamyl alcohol, indole, irone, isoeugenol, isoeugenol methyl ether, isosafrole, jasmone, camphor, carvacrol, carvone, p-cresol methyl ether, coumarin, p-methoxyacetophenone, methyl-n-amyl ketone, methylanthranilic acid methyl ester, p-methylacetophenone, methyl chavicol, p-methylquinoline, methyl beta naphthyl ketone, methyl-n-nonyl acetaldehyde, methyl-n-nonyl ketone, muscone, beta-naphthol ethyl ether, beta-naphthol methyl ether, nerol, nitrobenzene, n-nonyl aldehyde, nonyl alcohol, n-octyl aldehyde, p-oxyacetophenone, pentadecanolide, beta-phenylethyl alcohol, phenylacetaldehyde dimethyl acetal, phenylacetic acid, pulegone, safrole, salicylic acid isoamyl ester, salicylic acid methyl ester, salicylic acid hexyl ester, salicylic acid cyclohexyl ester, santalol, skatole, terpineol, thymene, thymol, gamma undelactone, vanillin, veratrum aldehyde, cinnamaldehyde, cinnamyl alcohol, cinnamic acid, cinnamic acid ethyl ester, cinnamic acid benzyl ester. Included among the more volatile fragrances are, in particular, the lower boiling-point scents of natural or synthetic origin, which can be used alone or in mixtures. Examples of more volatile scents are alkyl isothiocyanates (alkyl mustard oils), butanedione, limonene, linalool, linalyl acetate and linalyl propionate, menthol, menthone, methyl-n-heptenone, phellandrene, phenylacetaldehyde, terpinyl acetate, citral, and citronellal.

In accordance with a further preferred embodiment the agent according to the invention (i.e. the detergent or cleaning agent, cosmetic agent, or air freshening product) comprises at least one, preferably more than one, active components, in particular components having washing, care-providing or cleaning activity and/or cosmetic components, which are advantageously selected from the group comprising anionic surfactants, cationic surfactants, amphoteric surfactants, non-ionic surfactants, acidifying agents, alkalizing agents, anti-wrinkle compounds, antibacterial substances, antioxidants, antiredeposition agents, antistatic agents, builder substances, bleaching agents, bleach activators, bleach stabilizers, bleach catalysts, ironing aids, co-builders, shrinkage preventers, electrolytes, enzymes, color protectants, coloring agents, dyes, dye transfer inhibitors, fluorescent agents, fungicides, germicides, odor-complexing substances, adjuvants, hydrotropes, rinse aids, complexing agents, preservatives, corrosion inhibitors, water-miscible organic solvents, optical brighteners, perfume carriers, pearl luster pigments, pH adjusting agents, proofing and impregnating agents, polymers, swelling and anti-slip agents, foam inhibitors, sheet silicates, soil-repelling substances, silver protectants, silicone oils, soil-release active substances, UV-protection substances, viscosity regulators, thickening agents, discoloration inhibitors, graying inhibitors, vitamins and/or fabric-softeners. Within the meaning of this invention, values for the agent according to the invention in % by weight refer, unless otherwise indicated, to the total weight of the agent according to the invention.

The amounts of the individual ingredients in the agents according to the invention (i.e. detergents or cleaning agents, cosmetic agents or air freshening products) are each oriented toward the intended use of the agent in question, and a person skilled in the art is familiar in principle with the orders of magnitude of the amounts to be used of the ingredients or can deduce this from the associated technical literature. Depending on the intended use of the agents according to the invention, the surfactant content by way of example can be selected to be higher or lower. For example, the surfactant content for example of detergents can usually be between 10 and 50% by weight, preferably between 12.5 and 30% by weight, and in particular between 15 and 25% by weight, whereas for example cleaning agents for automatic dishwashing can include, for example, between 0.1 and 10% by weight, preferably between 0.5 and 7.5% by weight, and in particular between 1 and 5% by weight of surfactants.

The agents according to the invention (i.e. detergents or cleaning agents, cosmetic agents or air freshening products) can include surfactants, wherein anionic surfactants, non-ionic surfactants, and mixtures thereof are preferred, but cationic surfactants can also be considered. Suitable non-ionic surfactants are in particular ethoxylation and/or propoxylation products of alkyl glycosides and/or linear or branched alcohols having 12 to 18 C atoms in the alkyl moiety and 3 to 20, preferably 40 to 10 alkyl ether groups. Furthermore, corresponding ethoxylation and/or propoxylation products of N-alkyl amines, vicinal diols, fatty acid esters and fatty acid amides which correspond to the specified long-chain alcohol derivatives in terms of the alkyl moiety, and also of alkyl phenols having 5 to 12 C atoms in the alkyl group, can be used.

Suitable anionic surfactants are in particular soaps and those which include sulfate or sulfonate groups with preferably alkali ions as cations. Soaps that can be used are preferably the alkali salts of saturated or unsaturated fatty acids having 12 to 18 C atoms. Fatty acids of this type also cannot be used in completely neutralized form. The usable surfactants of the sulfate type include the salts of sulfuric acid half esters of fatty alcohols having 12 to 18 C atoms and the sulfation products of the specified non-ionic surfactants having a low degree of ethoxylation. The usable surfactants of the sulfonate type include linear alkyl benzene sulfonates having 9 to 14 C atoms in the alkyl moiety, alkanesulfonates having 12 to 18 C atoms, and olefin sulfonates having 12 to 18 C atoms, which are produced when corresponding monoolefins are reacted with sulfur trioxide, and also alpha sulfo fatty acid esters, which are produced with sulfonation of fatty acid methyl or ethyl esters.

Cationic surfactants are preferably selected from the esterquats and/or the quaternary ammonium compounds (QACs) of the general formula $(R^I)(R^{II})(R^{III})(R^{IV})N^+X^-$, in which $R^I$ to $R^{IV}$ are identical or different $C_{1-22}$ alkyl groups, $C_{7-28}$ aryl groups or heterocyclic groups, wherein two or, in the case of an aromatic incorporation as in pyridine, even three groups, together with the nitrogen atom form the heterocycle, for example a pyridinium or imidazolinium compound, and $X^-$ denotes halide ions, sulfate ions, hydroxide ions or similar anions. QACs can be prepared by reacting tertiary amines with alkylating agents, such as methyl chloride, benzyl chloride, dimethyl sulfate, dodecyl bromide, but also ethylene oxide. The alkylation of tertiary amines having one long alkyl group and two methyl groups is particularly easy, and the quaternization of tertiary amines having two long groups and one methyl group can also be carried out with the aid of methyl chloride under mild conditions. Amines which have three long alkyl groups or hydroxy-substituted alkyl groups lack reactivity and are, for example, quaternized with dimethyl sulfate. Eligible QACs are, for example, benzalkonium chloride (N-alkyl N,N-dimethyl benzyl ammonium chloride), benzalkone B (m,p-dichloro benzyl dimethyl-$C_{12}$-alkyl ammonium chloride, benzoxonium chloride (benzyl-dodecyl-bis-(2-hydroxyethyl) ammonium chloride), cetrimonium bromide (N-hexadecyl-N,N-trimethyl ammonium bromide), benzetonium chloride (N,N-dimethyl-N[2-[2-[p-(1,1,3,3-tetramethylbutyl)phenoxy]ethoxy]ethyl]benzyl ammonium chloride), dialkyldimethylammonium chlorides, such as di-n-decyldimethylammonium chloride, didecyldimethylammonium bromide, dioctyldimethylammonium chloride, 1-cetylpyridinium chloride, and thiazoline iodide, as well as mixtures thereof. Preferred QACs are the benzalkonium chlorides having $C_{8-22}$ alkyl residues, in particular $C_{12}$-$C_{14}$ alkylbenzyldimethylammonium chloride.

Preferred esterquats are methyl-N-(2-hydroxyethyl)-N,N-di(tallow-acyl-oxyethyl)ammonium methosulfate, bis (palmitoyl)ethyl hydroxyethyl methylammonium methosulfate or methyl-N,N-bis(acyloxyethyl)-N-(2-hydroxyethyl) ammonium methosulfate. Commercially available examples are the methyl hydroxyalkyl dialkoyloxyalkylammonium methosulfates marketed by Stepan with the trademark Stepantex or the products from BASF SE known by the trade name Dehyquart® or the products from the manufacturer Evonik Industries AG known by the name Rewoquat.

Surfactants are included in the agents according to the invention (i.e. detergents or cleaning agents, cosmetic agents or air freshening products) in quantitative proportions from preferably 5% by weight to 50% by weight, in particular from 8% by weight to 30% by weight. In laundry post-treatment agents in particular, preferably up to 30% by weight, in particular 5% by weight to 15% by weight surfactants, among these preferably at least a proportion of cationic surfactants, are used.

An agent according to the invention, in particular a washing or cleaning agent, preferably includes at least one water-soluble and/or water-insoluble, organic and/or inorganic builder. The water-soluble organic builder substances include polycarboxylic acids, in particular citric acid and sugar acids, monomeric and polymeric aminopolycarboxylic acids, in particular methylglycinediacetic acid, nitrilotriacetic acid and ethylenediaminetetraacetic acid as well as polyaspartic acid, polyphosphonic acids, in particular aminotris(methylenephosphonic acid), ethylenediaminetetrakis (methylenephosphonic acid) and 1-hydroxyethane-1,1-diphosphonic acid, polymeric hydroxy compounds, such as dextrin, and polymeric (poly)carboxylic acids, polymeric acrylic acids, methacrylic acids, maleic acids and copolymers of these, which can also include small proportions of polymerizable substances without carboxylic acid functionality polymerized into them. Suitable, although less preferred, compounds from this class are copolymers of acrylic acid or methacrylic acid with vinyl ethers, such as vinyl methyl ethers, vinyl esters, ethylene, propylene and styrene, in which the proportion of acid is at least 50% by weight.

The organic builder substances, in particular in order to produce liquid agents, can be used in the form of aqueous solutions, preferably in the form of 30 to 50% by weight aqueous solutions. All specified acids are used generally in the form of their water-soluble salts, in particular their alkali salts.

Organic builder substances, if desired, can be used in amounts of up to 40% by weight, in particular up to 25% by weight and preferably from 1% by weight to 8% by weight. Amounts close to the above upper limit are preferably used in paste-like or liquid, in particular aqueous, agents according to the invention. Laundry post-treatment agents, such as fabric softeners, can optionally also be free from organic builder.

Suitable as water-soluble inorganic builder materials are, in particular, alkali silicates and polyphosphates, preferably sodium triphosphate. In particular, crystalline or amorphous alkali aluminosiliates, if desired, can be used as water-insoluble, water-dispersible, inorganic builder materials in amounts of up to 50% by weight, preferably no more than 40% by weight, and in liquid agents in particular from 1% by weight to 5%. These include the crystalline sodium aluminosiliates in detergent quality, in particular zeolites A, P and optionally X are preferred. Amounts close to the specified upper limits are preferably used in solid agents provided in particulate form. Suitable aluminosiliates in particular have no particles having a particle size greater than 30 μm and preferably consist in a proportion of at least 80% by weight of particles having a size smaller than 10 μm.

Suitable substitutes or partial substitutes for the aforesaid aluminosilicate are crystalline alkali silicates, which may be present alone or mixed with amorphous silicates. The alkali silicates usable as builders in the agents according to the invention preferably have a molar ratio of alkali oxide to $SiO_2$ below 0.95, in particular from 1:1.1 to 1:12, and may be in amorphous or crystalline form. Preferred alkali silicates are the sodium silicates, in particular the amorphous sodium silicates, with a molar ratio $Na_2O:SiO_2$ from 1:2 to 1:2.8. The crystalline silicates, which may be present alone or mixed with amorphous silicates, are preferably crystalline sheet silicates of the general formula $Na_2Si_xO_{2x+1} \cdot y\, H_2O$), in which x, or what is known as the modulus, is a number from 1.9 to 4 and y is a number from 0 to 20, preferred values for x being 2, 3 or 4. Preferred crystalline sheet silicates are those in which x in the aforesaid general formula assumes the value 2 or 3. In particular, both beta and delta sodium disilicates ($Na_2Si_2O_5$ y $H_2O$) are preferred. Practically anhydrous crystalline alkali silicates of the abovementioned general formula manufactured from amorphous alkali silicates, in which x is a number from 1.9 to 2.1, may also be used in the agents according to the invention. In a further preferred embodiment of the agents according to the invention, a crystalline sodium sheet silicate with a modulus of 2 to 3 is used, as can be manufactured from sand and soda. Crystalline sodium silicates having a modulus in the range from 1.9 to 3.5 are used in a further preferred embodiment of agents according to the invention. If alkali aluminosilicate, in particular zeolite, is also present as an additional builder substance, the ratio by weight of aluminosilicate to silicate, in each case in relation to anhydrous active substances, is preferably from 1:10 to 10:1. In agents including both amorphous and crystalline alkali silicates, the ratio by weight of amorphous alkali silicate to crystalline alkali silicate is preferably 1:2 to 2:1 and especially 1:1 to 2:1.

Builder substances are included, if desired, in the agents according to the invention preferably in amounts up to 60% by weight, in particular from 5% by weight to 40% by weight. Laundry treatment agents according to the invention, such as fabric softeners, are preferably free from inorganic builder.

Peroxygen compounds that are suitable are, in particular, organic peroxy acids or peroxy acid salts of organic acids, such as phthalimidoperoxycaproic acid, peroxybenzoic acid, or salts of diperoxydodecanedioic acid, hydrogen peroxide and inorganic salts that release hydrogen peroxide under application conditions, such as perborate, percarbonate and/or persilicate. If solid peroxygen compounds are used, these can be used in the form of powders or granulates, which can also be encased, as is known in principle. Alkali percarbonate, alkali perborate monohydrate, or, especially in liquid agents, hydrogen peroxide are particularly preferably used, as appropriate, in the form of aqueous solutions, which include 3% by weight to 10% by weight of hydrogen peroxide. If an agent according to the invention includes bleaches, preferably such as peroxygen compounds, these are provided preferably in amounts of preferably up to 50% by weight, in particular 5% by weight to 30% by weight. The addition of small amounts of known bleach stabilizers, for example phosphonates, borates or metaborates and metasilicates and magnesium salts such as magnesium sulfate, may be expedient.

Compounds which are provided under perhydrolysis conditions of aliphatic peroxycarboxylic acids having preferably 1 to 10 C atoms, in particular 2 to 4 C atoms, and/or optionally substituted perbenzoic acid can be used as bleach activators. Suitable substances are those which carry O- and/or N-acyl groups of said C-atom number and/or optionally substituted benzoyl groups. Preference is given to plurally acylated alkylenediamines, in particular tetraacetylethylenediamine (TAED), acylated triazine derivatives, in particular 1,5-diacetyl-2,4-dioxohexahydro-1,3,5-triazine (DADHT), acylated glycolurils, in particular tetraacetylglycoluril (TAGU)N-acylimides, in particular N-nonanoylsuccinimide (NOSI), acylated phenol sulfonates, particularly n-nonanoyl or isononanoyloxybenzenesulfonate (n- or iso-NOBS), carboxylic acid anhydrides, in particular phthalic acid anhydride, acylated polyvalent alcohols, especially triacetin, ethylene glycol diacetate, 2,5-diacetoxy-2,5-dihydrofuran and enol esters and acetylated sorbitol and mannitol or mixtures thereof (SORMAN), acylated sugar derivatives, in particular pentaacetylglucose (PAG), pentaacetylfructose, tetraacetylxylose and octaacetyllactose, and acetylated, optionally N-alkylated glucamine and gluconolactone, and/or N-acylated lactams, for example N-benzoyl caprolactam. Hydrophilically substituted acyl acetals and acyl lactams are also preferably used. Combinations of conventional bleach activators may also be used. Such bleach activators can be included in the usual amount ranges, preferably in amounts from 1% by weight to 10% by weight, in particular 2% by weight to 8% by weight, in relation to the total agent.

In addition to the above-listed conventional bleach activators or instead of them, sulfonimines and/or bleach-boosting transition metal salts or transition metal complexes can also be included as what are known as bleach catalysts.

Suitable enzymes usable in the agents are those from the class of the proteases, cutinases, amylases, pullulanases, hemicellulases, cellulases, lipases, oxidases, and peroxidases, as well as mixtures thereof. Enzymatic active substances obtained from fungi or bacteria, such as *Bacillus subtilis, Bacillus licheniformis, Streptomyces griseus, Humicola lanuginosa, Humicola insolens, Pseudomonas pseudoalcaligenes,* or *Pseudomonas cepacia,* are particularly suitable. The enzymes that are optionally used can be adsorbed onto carrier substances and/or embedded in encapsulating substances in order to protect them from premature inactivation. They are included in the agents according to the present invention, if desired, preferably in amounts no greater than 5% by weight, in particular from 0.2% by weight to 2% by weight.

The agents can include, optionally, as optical brighteners, for example derivatives of diaminostilbene disulfonic acid or alkali metal salts thereof. For example, salts of 4,4'-bis (2-anilino-4-morpholino-1,3,5-triazinyl-6-amino) stilbene-2,2'-disulfonic acid or compounds of similar structure which, instead of the morpholino group carry a diethanolamino group, a methylamino group, an anilino group or a 2-methoxyethylamino, are suitable.

Suitable foam inhibitors include, for example, organopolysiloxanes and mixtures thereof with microfine, optionally silanized silica and paraffin waxes and mixtures thereof with silanized silica or bis-fatty acid alkylene diamides. Mixtures of various foam inhibitors are also advantageously used, for example mixtures of silicones, paraffins or waxes. The foam inhibitors, in particular foam inhibitors including silicone and/or paraffin, are preferably bonded to a granular carrier substance soluble or dispersible in water. Mixtures of paraffin waxes and bistearyl ethylene diamides are preferred in particular.

In addition, the agents may also include components which positively influence the oil and grease drain washability from textiles, or what are known as soil release active substances. This effect becomes particularly clear when a textile is soiled which has already been repeatedly washed beforehand with an agent including this oil- and fat-dissolving component. Preferred oil- and fat-dissolving components include, for example, non-ionic cellulose ethers such as methylcellulose and methyl hydroxypropyl cellulose with a proportion of methoxyl groups from 15 to 30% by weight and of hydroxypropoxyl groups from 1 to 15% by weight, in each case in relation to the non-ionic cellulose ether, as well as the polymers of phthalic acid and/or terephthalic acid known from the prior art or derivatives thereof with monomeric and/or po-meric diols, in particular polymers of ethylene terephthalates and/or polyethylene glycol terephthalates or anionically and/or non-ionically modified derivatives thereof.

The agents can also include color transfer inhibitors, preferably included in amounts from 0.1% by weight to 2% by weight, in particular 0.1% by weight to 1% by weight, which in a preferred embodiment of the invention are polymers of vinylpyrrolidone, vinylimidazole, vinylpyridine-N-oxide or copolymers thereof.

Graying inhibitors have the task of keeping the dirt detached from the textile fiber suspended in the washing liquor. Water-soluble colloids of usually organic nature are suitable for this purpose, for example starch, glue, gelatin, salts of ether carboxylic acids or ether sulfonic acids of starch or of cellulose or salts of acidic sulfuric acid esters of cellulose or starch. Water-soluble polyamides having acidic groups are also suitable for this purpose. Furthermore, apart from the above-mentioned starch derivatives, aldehyde starches can be used, for example. Cellulose ethers, such as carboxymethyl cellulose (Na salt), methyl cellulose, hydroxyalkyl cellulose and mixed ethers, such as methylhydroxyethyl cellulose, methylhydroxypropyl cellulose, methylcarboxymethyl cellulose and mixtures thereof can preferably be used, for example in amounts from 0.1 to 5% by weight in relation to the agents.

The organic solvents that can be used in the agents according to the invention, in particular when these are present in liquid or pasty form, include alcohols having 1 to 4 C atoms, in particular methanol, ethanol, iso-propanol and tert. butanol, diols having 2 to 4 C atoms, in particular ethylene glycol and propylene glycol, and mixtures thereof and the ethers derivable from the aforementioned compound classes. Water-miscible solvents of this type are provided in the agents according to the invention preferably in amounts of no more than 30% by weight, in particular from 6% by weight to 20% by weight.

To set a desired pH value produced by the mixture of the other components rather than spontaneously, the agents according to the invention can include system-compatible and environment-compatible acids, in particular citric acid, acetic acid, tartaric acid, malic acid, lactic acid, glycolic acid, succinic acid, glutaric acid and/or adipic acid, but also mineral acids, in particular sulfuric acid, or bases, in particular ammonium hydroxide or alkali hydroxides. Such pH regulators are optionally included in the agents according to the invention preferably in amounts not greater than 20% by weight, in particular from 1.2% by weight to 17% by weight.

The production of solid agents according to the invention (i.e. in particular detergents or cleaning agents) is not difficult and in principle can be implemented as is known by spray drying or granulation, for example, wherein optional peroxygen compound and optional bleach catalyst are added later, where appropriate. In order to produce agents according to the invention having an increased bulk density, in particular in the range from 650 g/l to 950 g/l, a method having an extrusion step is preferred. The production of liquid agents according to the invention likewise is not difficult and likewise can be implemented in a known manner.

The production of the ketones according to the invention is described by way of example in the examples section on the basis of the production of a pro-fragrance containing delta damascone. The other ketones of general formula (I) can also be obtained by the principle of this synthesis route.

In accordance with a preferred embodiment the teaching according to the invention can be used to reduce the proportion of perfume in detergents, cleaning agents and body care products significantly. As a result, it is possible to offer perfumed products even for those particularly sensitive consumers who, because of specific incompatibilities and irritations, can use normally perfumed products only to a limited extent or not at all.

A preferred solid, in particular powdered, detergent according to the invention can also include, in addition to the ketone according to the invention, in particular components that are selected for example from the following:
- anionic surfactants, such as preferably alkylbenzene sulfonate, alkyl sulfate, for example in amounts of preferably 5-30% by weight
- non-ionic surfactants, such as preferably fatty alcohol polyglycol ether, alkyl polyglucoside, fatty acid glucamide, for example in amounts of preferably 0.5-15% by weight
- builders, such as zeolite, polycarboxylate, sodium citrate, in amounts of for example 0-70% by weight, advantageously 5-60% by weight, preferably 10-55% by weight, in particular 15-40% by weight,
- alkalis, such as sodium carbonate, in amounts of for example 0-35% by weight, advantageously 1-30% by weight, preferably 2-25% by weight, in particular 5-20% by weight, bleaching agents, such as sodium perborate, sodium percarbonate, in amounts of for example 0-30% by weight, advantageously 5-25% by weight, preferably 10-20% by weight, corrosion inhibitors, for example sodium silicate, in amounts of for example 0-10% by weight, advantageously 1-6% by weight, preferably 2-5% by weight, in particular 3-4% by weight, stabilizers, for example phosphonates, advantageously 0-1% by weight, foam inhibitor, for example soap, silicone oils, paraffins, advantageously 0-4% by weight, preferably 0.1-3% by weight, in particular 0.2-1% by weight, enzymes, for example proteases, amylases, cellulases, lipases, advantageously 0-2% by weight, preferably 0.2-1% by weight, in particular 0.3-0.8% by weight, graying inhibitor, for example carboxymethyl cellulose, advantageously 0-1% by weight, discoloration inhibitor, for example polyvinylpyrrolidone derivatives, preferably 0-2% by weight, adjusting agents, for example sodium sulfate, advantageously 0-20% by weight, optical brighteners, for example stilbene derivative, biphenyl derivative, advantageously 0-0.4% by weight, in particular 0.1-0.3% by weight, optionally further scents optionally water optionally soap optionally bleach activators optionally cellulose derivatives optionally soil repellents, in each case in % by weight in relation to the total agent.

In another preferred embodiment of the invention, the agent is present in liquid form, preferably in gel form. Preferred liquid washing or cleaning agents as well as cosmetics have water contents of, for example, 10-95% by weight, preferably 20-80% by weight, and in particular 30-70% by weight, in relation to the total agent. In the case of liquid concentrates, the water content can also be particularly low, for example <30% by weight, preferably <20% by weight, in particular <15% by weight, in each case in relation to the total agent. The liquid agents can also include non-aqueous solvents.

A preferred liquid, in particular gel-like detergent according to the invention can also include, in addition to the ketone according to the invention, in particular components that are selected for example from the following:

anionic surfactants, such as preferably alkylbenzene sulfonate, alkyl sulfate, for example in amounts of preferably 5-40% by weight non-ionic surfactants, such as preferably fatty alcohol polyglycol ether, alkyl polyglucoside, fatty acid glucamide, for example in amounts of preferably 0.5-25% by weight builders, such as polycarboxylate, sodium citrate, advantageously 0-15% by weight, preferably 0.01-10% by weight, in particular 0.1-5% by weight, foam inhibitor, for example soap, silicone oils, paraffins, in amounts of for example 0-10% by weight, advantageously 0.1-4% by weight, preferably 0.2-2% by weight, in particular 1-3% by weight, enzymes, for example proteases, amylases, cellulases, lipases, in amounts of for example 0-3% by weight, advantageously 0.1-2% by weight, preferably 0.2-1% by weight, in particular 0.3-0.8% by weight, optical brighteners, for example stilbene derivative, biphenyl derivative, in amounts of for example 0-1% by weight, advantageously 0.1-0.3% by weight, in particular 0.1-0.4% by weight, optionally further scents, optionally stabilizers, water, optionally soap, in amounts of for example 0-25% by weight, advantageously 1-20 % by weight, preferably 2-15% by weight, in particular 5-10% by weight, optionally solvents (preferably alcohols), advantageously 0-25% by weight, preferably 1-20% by weight, in particular 2-15% by weight, % by weight in each case in relation to the total agent.

A preferred liquid fabric softener according to the invention can also include, in addition to the ketone according to the invention, in particular components that are selected from the following:

cationic surfactants, such as in particular esterquats, for example in amounts of 5-30% by weight, co-surfactants, such as for example glycerol monostearate, stearic acid, fatty alcohols, fatty alcohol ethoxylates, for example in amounts of 0-5% by weight, preferably 0.1-4% by weight, emulsifiers, such as for example fatty amine ethoxylates, for example in amounts of 0-4% by weight, preferably 0.1-3% by weight, optionally further scents dyes, preferably in the ppm range stabilizers, preferably in the ppm range solvents, such as water, in amounts of preferably 60-90% by weight, % by weight in each case in relation to the total agent.

The invention also relates to a cosmetic agent, wherein the cosmetic agent includes a ketone of general formula (I) according to the invention.

The invention also relates to a method for the long-lasting scenting of surfaces, wherein a ketone of general formula (I) according to the invention or a detergent or cleaning agent according to the invention is applied to the surface to be scented (for example textile, dishes, floor) and said surface is then exposed to an electromagnetic radiation comprising the wavelengths from 200 to 600 nm.

The invention also relates to a method for long-lasting room scenting, wherein an air freshening product according to the invention is exposed to an electromagnetic radiation comprising the wavelengths from 200 to 600 nm.

EXAMPLE 1

Synthesis of Benzoyl Acetic Acid Ethyl Ester

Illustration of a ketone of general formula (I):

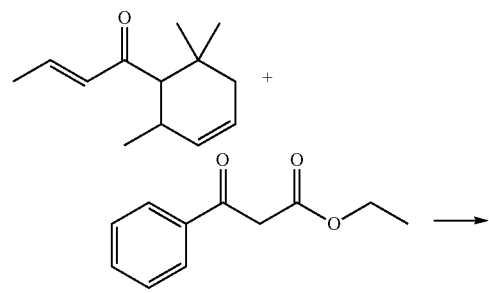

-continued

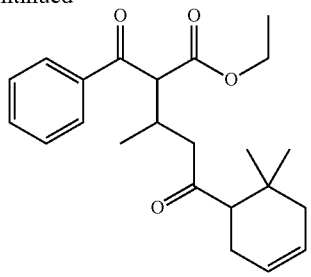

17.3 g (90 mmol) of benzoyl acetic acid ethyl ester (CAS No.: 94-92-0) and delta damascone (90 mmol, CAS No.: 57378-68-4) were dissolved in 15 ml chloroform in a nitrogen atmosphere. 0.24 g iron (III) chloride □ 6H$_2$O (0.9 mmol) were then added, whereby the solution immediately turned brown in color.

The solution was stirred for 24 h, then the solution was filtered. The red-brown raw product was dissolved in chloroform and filtered again over a column filled with neutral aluminum oxide.

28.2 g of orange-colored, clear, viscous product were obtained.

$^1$H-NMR (CDCl$_3$): m 8.0 (2H); m 7.6 (1H); m 7.5 (2H); m 5.5 (1H); dbr 5.4 (1H); m 4.6 (1H); m 4.1 (2H); 2.9 (2H); m 2.6-2.5 (2H); m 2.2 (1H); m 1.9 (1H); m 1.7 (1H); m 1.1-0.9 (12H), dd (3H).

IR; 3500, 3000, 1739, 1705, 1687, 1598, 1580.

The ketone produced in this way demonstrated a very good fragrancing effect when used in detergents and fabric softeners in the case of textile treatment. In particular, an improved longevity of the perceived fragrance on the laundry washed and then dried therewith was found compared with detergents and fabric softeners including an equivalent amount of delta damascone, but otherwise of identical composition. The perceived fresh fragrance of the textiles was present for much longer, both after line drying and in particular after drying in a tumble dryer.

EXAMPLE 2

Benzyl-2-benzoyl-3-methyl-5-oxo-5-(2,6,6-trimethylcyclohex-3-enyl)-pentanoate

1$^{st}$ Stage Benzoyl Acetic Acid Benzyl Ester

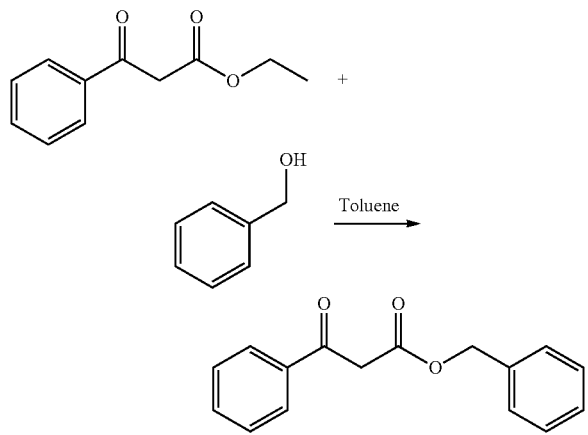

7.45 mmol benzoyl acetic acid ethyl ester and 8.90 mmol benzyl alcohol were dissolved in 50 ml toluene in a 100 ml round-bottomed flask and heated for 24 h to reflux. The reaction mixture was then cooled to room temperature and the solvent was removed at reduced pressure. The product was used in the next stage without further purification.

2$^{nd}$ Stage:

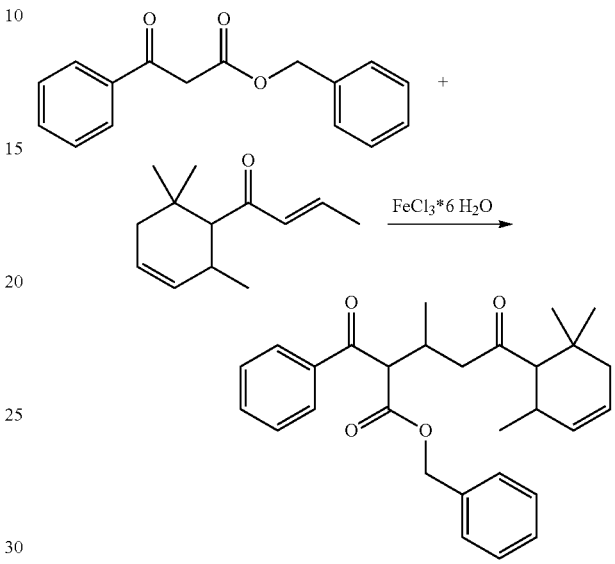

Formula (IX)

A mixture of 12 mmol benzoyl acetic acid benzyl ester, 12 mmol δ damascone and 2.4 mmol iron (III) chloride hexahydrate was stirred in a 25 ml round-bottomed flask for 24 h at 50° C. The raw product was then purified by means of column chromatography (methyl-tert. butyl ether:cyclohexane, 1:4 R$_f$=0.41). The yield, in relation to the raw product used, was 80%.

EXAMPLE 3

Dodecyl-2-benzoyl-3-methyl-5-oxo-5-(2,6,6-trimethylcyclohexy-3-enyl)-pentanoate

1$^{st}$ Stage Benzoylacetic Acid Dodecyl Ester

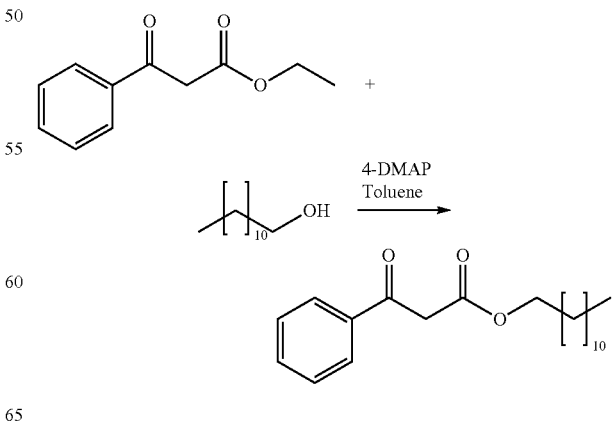

10 mmol benzoyl acetic acid ethyl ester, 11.9 mmol 1-dodecanol and 1 mmol 4-dimethylaminopryridine were placed in 50 ml toluene in a 100 ml round-bottomed flask. The resultant ethanol was distilled off with the solvent. The resultant product was purified by means of column chromatography (acetoacetic acid:cyclohexane: 1:10, $R_f$=0.52), wherein the yield was 76%.

$2^{nd}$ Stage

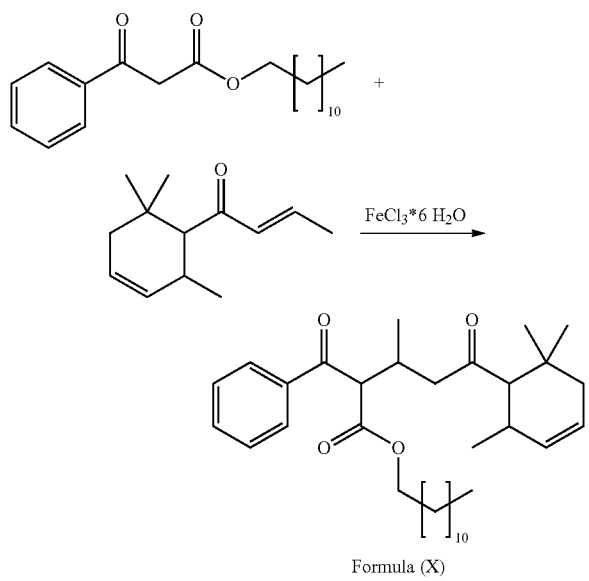

Formula (X)

A mixture of 10 mmol benzoyl acetic acid benzyl ester, 10 mmol δ damascone and 1 mmol iron (III) chloride hexahydrate was stirred in a 25 ml round-bottomed flask for 24 h at 50° C. The raw product was then purified by means of column chromatography (methyl-tert. butyl ether:cyclohexane, 1:4 $R_f$=0.43). The yield was 72%.

EXAMPLE 4

Release Behavior

The test substances were formulated into a fabric softener in equal molar amount compared with the scent included therein, and said fabric softener was used in the rinsing stage of a washing process. The laundry treated in this way was exposed, after drying, to sunlight for 1 to 7 h and was then smelt by ten olfactorily trained individuals, wherein each sample was assessed in two independent tests. The fragrance intensity was indicated by a scale from 1 to 10 (10: very strong, 1: very weak).

The pure scent delta damascone (reference) and the compound of formula (XI) known from the prior art formula XI

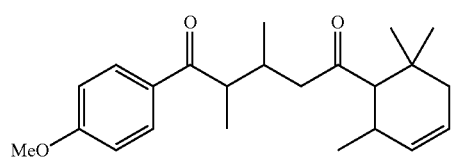

and the ketones of formulas (IV) and (X) were examined:

| Sample | Dosing [% by weight] | Fragrance intensity after 1 h in the sun | Fragrance intensity after 3 h in the sun | Fragrance intensity after 5 h in the sun | Fragrance intensity after 7 h in the sun |
|---|---|---|---|---|---|
| Reference | 0.4 | 3 | 2 | 1 | 2 |
| Ketone XI | 0.74 | 3 | 3 | 3 | 3 |
| Ketone IV | 0.80 | 6 | 6 | 6 | 7 |
| Ketone X | 1.65 | 7 | 6 | 7 | 7 |

It was found that the compound according to the invention is superior to the known substances in view of the fragrance intensity.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A compound of general formula (I)

formula (I)

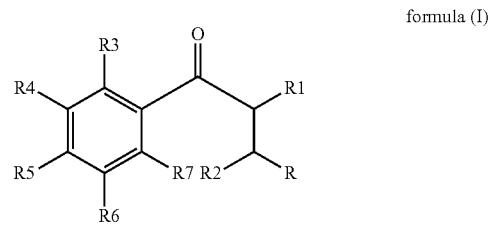

wherein
R is a substituted hydrocarbon group, which has at least one C=O group or an ester group;
R1 is —COX;
R2 is a linear or branched, substituted or unsubstituted alkyl group having 3 C atoms;
R3, R4, R5, R6 and R7, independently of one another, are hydrogen, a halogen atom, an amino group, —NO2, —NH alkyl, —N(alkyl)$_2$, a linear or branched, substituted or unsubstituted alkoxy group having up to 15 C atoms, or a linear or branched, substituted or unsubstituted alkyl group having up to 15 C atoms, a cycloalkyl group, an acyl group, an aryl group, —OH, —COY group, or a quaternary ammonium group of formula (II)

(II)

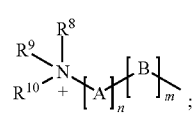

X is H, —R11, —OR11, —NR11R12, —SR11 or halogen;
Y is hydrogen, alkyl, cycloalkyl, aryl, acyl, —OH, —Oalkyl, —NH$_2$, NH-alkyl, —N(alkyl)$_2$ or halogen, A is a $CH_2$ group or a $CH_2CH_2O$ group with n=1 to 20;

B is oxygen with m=0 or 1, wherein m=0 when A is a $CH_2CH_2O$ group;

R8, R9 and R10, independently of one another, are H or a substituted or unsubstituted group including alkyl, cycloalkyl, alkenyl, aryl or acyl groups, and wherein two of the groups R8, R9 and R10 can be interconnected by ring closure; and R11 and R12, independently of one another, are hydrogen, a linear or branched, substituted or unsubstituted alkyl, aryl, alkylaryl, arylalkyl or alkenyl group, which can all optionally contain heteroatoms, and wherein R13, R14 and R15, independently of one another, are hydrogen, or a linear or branched, substituted or unsubstituted alkyl group.

2. The compound according to claim 1, wherein R2 is a linear or branched, substituted or unsubstituted alkyl group having up to 6 C atoms.

3. The compound according to claim 1, wherein R2 is a methyl group.

4. The compound according to claim 1, wherein R3, R4, R5, R6 and/or R7 denote hydrogen.

5. The compound according to claim 1, wherein R3, R4, R5, R6 and R7 denote hydrogen.

6. A compound having a formula selected from the group consisting of (IV) to (X):

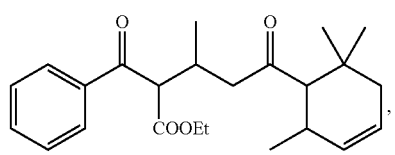
(IV)

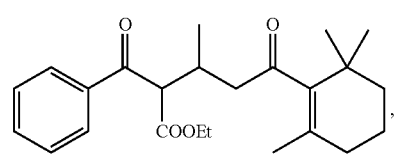
(V)

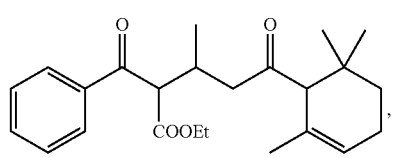
(VI)

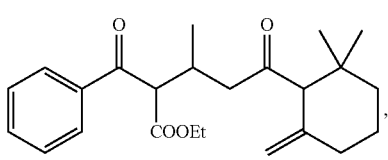
(VII)

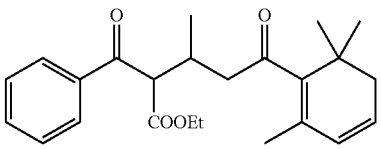
(VIII)

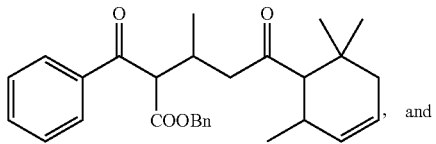
(IX) , and

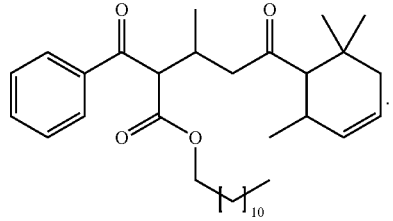
(X)

7. A detergent or cleaning agent, comprising at least one compound of claim 1.

8. A detergent or cleaning agent according to claim 7, wherein the compound of claim 1 comprises 0.0001 and 5% by weight of the total agent.

9. A detergent or cleaning agent according to claim 7, wherein the compound of claim 1, comprises between 0.01 and 3% by weight of the total agent.

10. The detergent or cleaning agent according to claim 7, wherein it further comprises
 (1) it includes at least one surfactant, selected from the group consisting of anionic, cationic, non-ionic, zwitterionic or amphoteric surfactants, or mixtures thereof; and/or
 (2) the detergent or cleaning agent is in solid or liquid form.

11. An air freshening product, comprising at least one compound of claim 1.

12. An air freshening product according to claim 11, wherein the compound of claim 1 comprises 0.0001 and 50% by weight of the total product.

13. An air freshening product according to claim 11, wherein the compound of claim 1 comprises 0.01 and 3% by weight of the total product.

14. A cosmetic agent, comprising at least one compound of claim 1.

15. A cosmetic agent according to claim 14, wherein the compound of claim 1 comprises 0.0001 and 5% by weight of the total agent.

16. A cosmetic agent according to claim 14, wherein the compound of claim 1 comprises 0.01 and 3% by weight of the total agent.

* * * * *